United States Patent [19]

Klemann et al.

[11] 4,169,808

[45] Oct. 2, 1979

[54] HALOORGANOMETALLIC LITHIUM SALT COMPLEX COMPOSITIONS AND ELECTROLYTE COMPOSITIONS CONTAINING THESE

[75] Inventors: Lawrence P. Klemann, Somerville; Gerald H. Newman, Westfield; Eugene L. Stogryn, Edison, all of N.J.

[73] Assignee: Exxon Research & Engineering Co., Florham Park, N.J.

[21] Appl. No.: 882,805

[22] Filed: Mar. 2, 1978

[51] Int. Cl.$^2$ .................. H01M 6/14; H01M 6/16
[52] U.S. Cl. .................. 252/182.1; 252/518; 423/179.5; 429/213; 429/218
[58] Field of Search .................. 252/182.1, 518; 423/179.5; 429/213, 218

[56] References Cited

U.S. PATENT DOCUMENTS

| | | | |
|---|---|---|---|
| 3,734,963 | 5/1973 | Langer et al. | 260/563 R |
| 3,764,385 | 10/1973 | Langer et al. | 429/194 |
| 4,060,674 | 11/1977 | Klemann et al. | 429/194 |

OTHER PUBLICATIONS

Bhattacharyya et al., J. Phys. Chem, vol. 69, (1965), p. 608.
Brenner; A., Advances in Electrochemistry and Electrochemical Eng., Interscience, 1967, p. 214.
Chambers; R. D., J. Am. Ch. Soc., vol. 82, (Oct. 20, 1960), pp. 5298-5301.
Brauer et al., Inorganic Chem., vol. 16, No. 9, (1977), pp. 2305-2314.
Chan, et al., Can. Jou. of Chem., vol. 46, (1968), pp. 1237-1248.
Muetterties et al., Inorganic Chem., vol. 4, (1965), pp. 119-121.
Vandenberg et al., Anal. Chimica, Acta, vol. 44, (1969), pp. 175-183.
Massey et al., J. Organometal. Chem., vol. 2, (1964), pp. 245-250.
Seyforth et al., J. Organometallic Chem., vol. 141, (1977), pp. 71-83).
Ahmed et al., Inorganic Chem., vol. 7, (1969), pp. 1411-1413.

*Primary Examiner*—Benjamin R. Padgett
*Assistant Examiner*—Irwin Gluck
*Attorney, Agent, or Firm*—Kenneth P. Glynn

[57] ABSTRACT

Novel compositions are described which comprise halogenated organometallic lithium salt complexes having the formula $LiMR_nX_i$ wherein M is a metal selected from the group consisting of Zn, Cd, B, Al, Ga, In, Tl, Sn (stannous), P and As, the Rs are specified haloorganic radicals, the Xs are selected from various halides, alkyls, aryls, alkaryls and aralkyls, and n and i are numerical values, the sum of which is equal to one plus the valence of the metal M, subject to the provisos that if n is zero, at least one X is an organic radical and that if i is zero, not all R radicals are perhalogenated aryl radicals. Also described are electrolyte compositions for electrochemical cells which contain electrolytically active lithium salt complexes including these novel compositions of matter.

39 Claims, No Drawings

HALOORGANOMETALLIC LITHIUM SALT COMPLEX COMPOSITIONS AND ELECTROLYTE COMPOSITIONS CONTAINING THESE

BACKGROUND OF THE INVENTION

1. Field of the Invention

The present invention relates to novel compositions of matter and electrolyte compositions for high energy density electrochemical cells including these compositions. More specifically, the present invention is directed to compositions of matter and to electrolyte compositions containing electrolytically active lithium salt complexes including these compositions, the compositions comprising haloorganometallic alkali metal salt complexes.

2. Prior Art

A recently developed rechargeable, high energy density electrochemical cell consists of an alkali metal material as the anode-active material, a transition metal chalcogenide as the cathode-active material, and a nonaqueous electrolyte. More specifically, preferred cells consist of lithium anodes, titanium disulfide cathodes and nonaqueous electrolyte compositions consisting of various lithium salts, such as $LiClO_4$, dissolved in organic solvents, such as propylene carbonate, tetrahydrofuran, dioxolane, and mixtures of dimethoxyethane and tetrahydrofuran, and containing various stabilizing additives.

Important features of these cells include their ability to be repeatedly discharged and charged. Theoretically, cycling by discharging and charging should be possible indefinitely, but in practice indefinite cycling is not realized. Dendritic growth on the anode during charging and degradation of the cathode material are sometimes limiting factors in the amount of cycling to which a cell can be subjected. However, the electrolyte, particularly nonaqueous electrolytes, can at times be the limiting factor. The effects of a particular electrolyte composition on the electrochemical performance of a cell may be significant due to its relative stability or it may be due to other factors. One particular electrolyte composition might be highly effective with a given anode-cathode couple but be ineffective for another couple, either because it is not inert to the second couple or because it reacts with itself under the conditions present during cycling. Furthermore, even when a particular electrolyte composition is effective in a given cell, it may nonetheless be undesirable for other reasons. For example, the sometimes preferred $LiClO_4$ based electrolyte creates a potential explosion hazard. And, for example, various organo-metallic alkali metal salt compounds such as are described in U.S. Pat. Nos. 3,734,963 and 3,764,385 have the disadvantage of requiring complexing with various nitrogen, phosphorus or sulfur-containing organic compounds containing at least two functionalities.

Recent studies have been made directed to $LiB(C_6H_5)_4$ electrolyte systems by Bhattacharyya et al, *J. Phys. Chem.*, Vol. 69, p 608 et seq. (1965) but these systems have been found to have low solubility and high resistivity. Additionally, mention has been made by A. Brenner that certain alkali metal organometallic salts have electrochemical properties, e.g. $NaB(C_2H_5)_4$ and $NaAl(C_2H_5)_4$, in *Advances in Electrochemistry and Electrochemical Engineering*, Vol. 5, at page 214. Also, Chambers et al, *JACS*, Vol. 82, (Oct. 20, 1960), pages 5298–5301, and Burger et al, *Inorganic Chem.*, Vol. 16, No. 9 (1977), pages 2305–2314 describe various alkali metal salts of the metaloorganic structure, including the fluorinated compound $KB(CF_3)F_3$. Vandeberg et al in *Anal. Chimica Acta*, Vol. 44, pp 175 et seq. (1969) describe various sodium salts such as $NaB(C_6H_4—p—F)_4$, $NaB(C_6H_4—m—F)_4$ and $NaB(C_6H_4—p—CF_3)_4$. However, none of these references teaches any electrochemical utility for these compounds or suggests that the compounds of the present invention even exist. Massay et al, *J. Organomet. Chem.*, Vol. 2 (February 14, 1964) pp. 245–250, describe the compounds $LiB(C_6F_5)_4$ and $KB(C_6F_5)_4$ but do not teach the compounds of the present invention or their use in electrolyte systems.

Seyferth et al, *J. Organometallic Chemistry*, Vol. 141, pp 71–83 (1977) describe the preparation of $LiB(C_6H_5)_3(CH_2CH=CCl_2)$. However, this compound differs from the present invention compounds in that it is unsaturated. The substituents on the central metal atom of the compounds described herein do not include halogenated alkenyl groups. Ahmed et al, *Inorganic Chemistry*, Vol. 8 pp. 1411–1413 (1969) describe $[(C_2H_5)_4N]^+[B(C_6H_5)Cl_3]^-$ in acetonitrile and report its conductivity, but do not teach an alkali metal analogue. Muetterties et al, *Inorganic Chemistry*, Vol. 4, pp. 119–121 (1965) use NMR to infer the existence of $H^+[P(CH_3)F_5]^-$ and $H^+[P(C_6H_5)F_5]^-$ in dimethylsulfoxide solution ($CH_3SOCH_3$), but do not teach the existence of alkali metal analogous. Chan et al, *Canadian Journal of Chemistry*, Vol. 46, pp. 1237–1248 (1968) describe the preparation of $Cs^+[P(CF_3)F_5]^-$ and $Cs^+[P(CF_3)_2F_4]^-$, and $Cs^+[P(CF_3)_3F_3]^-$, and $Ag^+[P(CF_3)_2F_4]^-$ and their properties in water and acetonitrile. However, no alkali metal analogous are described or suggested. U.S. Pat. No. 4,060,674, describes various alkali metal-metal-organic salts and their use in electrochemical cells, but haloorganic substituted salts are not taught.

In summary, it is believed that to date the novel compounds and electrolyte compositions of the present invention have not been heretofore disclosed or rendered obvious.

DESCRIPTION OF THE PRESENT INVENTION

The present invention is directed to novel compositions of matter and to improved electrolyte compositions containing these novel compositions of matter.

The compositions of matter of the present invention include haloorganometallic lithium salt complexes of the formula $$LiMR_nX_i \qquad (1)$$

wherein M is a metal selected from the group consisting of Zn, Cd, B, Al, Ga, In, Tl, Sn (stannous), P and As, R represents various haloorganic radicals, as set forth below, X represents various halides, alkyls, aryls, alkaryls and aralkyls, and n and i are numerical values, zero or greater, the sum of which is equal to one plus the valence of the metal M, subject to the provisos that, if n is zero, at least one X is an organic radical, and that, if i is zero, not all R radicals are perhalogenated aryl radicals.

The metal M is Formula (1) is any of zinc, cadmium, boron, aluminum, gallium, indium, thallium, tin (stannous), phosphorus and arsenic. Desirably, M is selected from the group consisting of boron, aluminum, thallium, phosphorus and arsenic. Preferred are boron, aluminum and phosphorus, and most preferred is boron.

The haloorganic radicals represented by each R may be the same or different and are inertly substituted or unsubstituted radicals selected from the group consisting of halogenated alkyls, halogenated aryls, halogenated alkaryls and halogenated aralkyls, subject to the proviso that the radicals are not alpha halogenated. By "inertly substituted" is meant radicals containing substitutents, in addition to the halogen substituents for haloorganic radicals, which have no detrimental effect on the electrolytic properties of the electrolyte compositions in the context of its effectiveness in electrochemical cells. When R constitutes or contains an alkyl moiety it is meant to be a fully saturated moiety. The radicals may be selected from the group consisting of halogenated alkyl radicals having 2 to 8 carbon atoms, halogenated aryl radicals having 6 to 18 carbon atoms, and halogenated alkaryl and halogenated aralkyl radicals having 7 to 50 carbon atoms, subject to the mentioned proviso. Desirably, these radicals are the halogenated alkaryl and halogenated aralkyl radicals having 7 to 25 carbon atoms, and the halophenyl radicals. Preferred are the radicals which are halogenated alkaryl radicals having 7 to 15 carbon atoms.

The radicals represented by the variable X in Formula (1) are selected from the group consisting of halides, alkyls, aryls, alkaryls and aralkyls. Thus, each X may be the same or different and may be, in the case of X being an organic radical, unsubstituted or inertly substituted, as defined above. The variable X may be, therefore, a halide, or it may be an inertly substituted or an unsubstituted organic radical, i.e., an alkyl radical, aryl radical, alkaryl radical or aralkyl radical. When X is one of the foregoing organic radicals, it may be selected from the group consisting of alkyls having 1 to 8 carbon atoms, aryls having 6 to 18 carbon atoms, and alkaryls and aralkyls having 7 to 50 carbon atoms. Desirably, X is a halogen or an organic radical selected from alkyls having 1 to 6 carbon atoms and the phenyl radical. Particularly useful is the methyl radical. When X is a halogen, it is desirably fluorine, chlorine, bromine, or iodine, and preferably is fluorine and chlorine.

The variables n and i in Formula (1) above are numerical values, the sum of which is equal to one plus the valence of the metal M. Thus, for example, $n+i=3$ when M is zinc, and, for example, $n+i=4$ when M is boron, and $n+i=6$ when M is phosphorus. Either n or i may be zero, but when n is zero, at least one X must be an organic radical and when i is zero, not all R radicals are perhalogenated aryl radicals.

All of the embodiments of Formula (1) above are necessarily haloorganometallic lithium salt complexes. Among the many complexes included in Formula (1) are the following generic types of complexes:

LiM { halogenated alkyl, halogenated aryl, halogenated alkaryl, halogenated aralkyl or combinations thereof }$_n$     (2)

LiM { halogenated alkyl, halogenated aryl, halogenated alkaryl, halogenated aralkyl or combinations thereof }$_n$ (halogen)$_i$     (3)

 (4)

 (5)

LiM { alkyl, aryl, alkaryl, aralkyl or combinations thereof }$_a$ (halogen)$_b$     (6)

wherein $a+b=i$, and wherein n and i are defined above.

Specific examples of the foregoing are as follows:

LiAl(C$_6$F$_5$)(CH$_2$CF$_3$)$_3$
LiBF$_3$(C$_6$H$_5$)
LiB[C(CF$_3$)$_3$]$_3$CH$_3$
LiAl(CH$_3$)$_3$CH$_2$CCl$_3$
LiB(CH$_3$)$_3$CH$_2$CCl$_3$
LiAl(CH$_3$)$_3$CH$_2$CF$_3$
LiPF$_4$(CH$_2$CF$_2$CH$_3$)$_2$
LiPF$_5$(C$_6$F$_5$)
LiB(C$_3$)$_3$CH$_2$CF$_3$
LiB(C$_6$H$_5$)$_3$(CH$_2$CF$_3$)
LiB(CH$_3$)$_3$(C$_6$H$_4$—m—CF$_3$)
LiB(C$_6$H$_4$—P—CF$_3$)$_4$
LiB(C$_6$H$_4$—m—CF$_3$)$_4$
LiB(C$_6$H$_4$—P—F)$_4$
LiB(C$_6$F$_5$)$_3$CH$_3$
LiB(C$_6$F$_5$)$_3$—n—C$_4$H$_9$
LiB(C$_6$H$_5$)$_3$C$_6$F$_5$
LiB(C$_6$H$_4$—p—CH$_3$)$_3$C$_6$F$_5$
LiB(C$_6$F$_5$)$_3$F
LiB(CH$_3$)$_2$(C$_6$H$_4$—p—CF$_3$)$_2$
LiB(C$_2$H$_5$)$_2$(C$_6$H$_4$—p—F)$_2$

The haloorganometallic lithium salt complexes of the present invention may be prepared by reacting lithium metal compounds of the formula:

$$LiR \quad (7)$$

with metal compounds of the formula:

$$MR_{n-1}X_i \quad (8)$$

wherein all of the variables are defined above. The principal reaction is believed to be represented by the following equation:

$$LiR + MR_{n-1}X_i \rightleftharpoons LiMR_nX_i \quad (A)$$

or in ionic terms:

$$LiR + MR_{n-1}X_i \rightleftharpoons Li^+[MR_nX_i]^- \quad (B)$$

wherein the variables are as defined for Formula (1) above.

In the alternative, the complexes of the present invention may be prepared by reacting lithium metal compounds of the formula:

LiX    (9)

with metal compounds of the formula:

$$MR_nX_{i-1} \quad (10)$$

wherein all of the variables are defined above. In this approach, it is believed that the principal reaction is represented by the following equation:

$$LiX + MR_nX_{i-1} \rightleftharpoons LiMR_nX_i \text{ or } Li^+[MR_nX_i]^- \quad (C)$$

wherein the variables are as defined for Formula (1) above.

In addition to the above preparation modes, many of the compounds of Formula (1) above may be prepared by using a compound prepared by the reaction of Equation (A), (B) or (C) above as a reactant, in combination with a lithium compound of either Formula (7) above, or Formula (9) above. These two reactions are represented by the forward and reverse reactions of Equation (D) as follows:

$$LiR + LiMR_nX_i \rightleftharpoons LiMR_{n+1}X_{i-1} + LiX \quad (D)$$

It should be noted that the reactions of Equation (D) may favor the forward or the reverse reaction depending upon the exact starting materials and the relative concentrations of the reactants.

In the alternative, compounds outside the scope of Formula (1) and, therefore, outside the scope of reaction products of Equation (A), (B) and (C), wherein n is zero, and contrary to the proviso, all Xs are halogens, may be used with Formula (7) and non-halogenated Formula (9) starting compounds as illustrated by Equations (E) and (F) respectively:

$$LiR + LiMX'_n \rightleftharpoons LiMX'_{n-1}R + LiX' \quad (E)$$

and, $$LiX'' + LiMX'_n \rightleftharpoons LiMX'_{n-1}X'' + LiX' \quad (F)$$

wherein X' is a halogen, X'' is any X except halogen, and all other variables are as described above.

In addition, it should be noted that the reactions represented by Equations (D), (E) and (F) above may be carried out using a Grignard reagent in place of the LiR, LiX, LiX' and LiX'' compounds. In other words, the monovalent lithium salt in which the lithium of that salt merely acts as a carrier and does not become part of the desired product compound may be replaced by a Grignard reagent carrier. This substitution is within the purview of the artisan.

In some of the above reactions, in addition to the desired reaction product, minor impurities may be formed. These impurities may be removed by laboratory washings with quarternary ammonium salt baths, the washes being repeated as necessary to achieve the desired purity.

These reactions may be carried out at any operable pressure and temperature and room temperature and pressure conditions will allow these reactions to readily occur in most instances. However, in some instances, undesirable side product of the aforementioned procedures may be advantageously circumvented by effecting the reaction at temperatures below ambient. For example, reaction temperatures in the range of about $-100°$ C. to about $25°$ C. may be used.

The electrolyte compositions of the present invention contain organic solvent and contain electrolytically active alkali metal salt complexes including the above-mentioned novel haloorganometallic lithium salt complexes represented by Formula (1), and may be utilized in electrochemical applications and devices such as batteries and other cells. In the novel electrolyte compositions of the present invention, the compositions of matter described above may be used singly or in combination with each other and/or with other compatible salts. Thus, an essential aspect of electrolyte compositions of the present invention is that at least one Formula (1) type salt complex be used in combination with organic solvent. Other salts which may optionally be included are any of the electrolytically active alkali metal salts which are compatible with the Formula (1) type salt complexes, e.g., LiBr, LiI and the like. As mentioned, also contemplated is the electrolyte which contains only one or more salt complexes of Formula (1). Thus, the expression "electrolytically active alkali metal salt complexes including haloorganometallic lithium salt complexes" should be construed to include: (1) mixtures of haloorganometallic lithium salt complex(es) and other compatible alkali metal salt(s), and (2) one or more haloorganometallic lithium salt complexes without other salt(s). Preferred is the electrolyte containing the haloorganometallic salt complex(es) without other salts.

The organic solvent which may be employed in the electrolyte compositions of the present invention is generally one which will be compatible with the complexes and the system in which it is used. These may be selected from the group consisting of inertly substituted and unsubstituted ethers, esters, alkylene carbonates, amines, amides, lactones, sulfones, organic sulfites, organic sulfates, orthoformates, alkylhaloformates, polyamines, organic nitro compounds and nitrites. By "inertly substituted" solvent is meant one which contains substituents which have no detrimental effect on the electrolytic properties of the electrolyte composition in the context of its effectiveness in electrochemical cells. These solvents may be any of the foregoing which will function as either a diluent or as a complexing solvent with the haloorganometallic lithium salt complex and which will, with the complex, produce an effective electrolyte. Thus, the solvents which are included are those composed of one or more compounds selected from straight chain ethers, polyethers, cyclical ethers, cyclicpolyethers, aminoethers and lactone ethers, including such ethers as the acetals, ketals and orthoesters; and organic esters, alkylene carbonates, amines, amides, lactones, sulfones, organic nitro compounds and nitrites, orthoformates, alkylhaloformates, polyamines, and organic sulfates and sulfites. Examples include propylene carbonate, tetrahydrofuran, dioxolane, furan, sulfolane, dimethyl sulfite, nitrobenzene, nitromethane, gamma butyrolactone and the like. The preferred solvents are the ethers. For example, dioxolane, 4-(methoxymethyl)dioxolane, dimethoxyethane, and mixtures of these are useful. Preferred is a solvent containing dioxolane.

In general, when a solvent is used, sufficient organic solvent may be included to enhance the haloorganometallic lithium salt complex electrolytical activity (i.e., increase conductivity) when employed in an electrolytic cell. There is no criticality to the amount of solvent present, although over dilution resulting in diminished electrochemical activity should be avoided. The solvent may be a mixture of compounds as suggested above, and may contain known electrolyte additives which are compatible with the solvent and the particular salt employed.

The compositions of matter and the electrolyte compositions of the present invention may be used in improved, rechargeable, high energy density electrochemical cells. The cells include any containing alkali metal anodes wherein the compositions of matter of the present invention are operable electrolytes. Particularly useful are the cells containing anodes having lithium as the anode-active material and cathodes having solid cathode-active materials, e.g. cathodes having transition metal chalcogenides. Also preferred are the secondary cells.

Alkali metals used in the anodes are desirably lithium, and alloys containing lithium, and the transition metal chalcogenide cathode-active materials include those containing at least one member selected from the group consisting of titanium, zirconium, hafnium, molybdenum, niobium, tantalum, vanadium, and iron; and at least one chalcogen selected from oxygen, sulfur, selenium, and tellurium. The anode is advantageously made of lithium or lithium alloys because lithium has the lowest equivalent weight of the alkali metals, is the most electronegative, thereby providing the most energy per weight unit and is most compatible with the lithium salts of the present invention. Of the lamellar transition metal chalcogenides, preferred are the dichalcogenides, and the most preferred is titanium disulfide because it has a low equivalent weight, is electrically conductive and its constituents are readily available. The electrolyte composition consists essentially of solvent and alkali metal salt(s) which is set forth above.

The following examples are presented as merely being illustrative of the present invention, and the invention should not be construed to be limited thereto. Examples 1, 2 and 3 are directed to prior art compounds and Examples 4 to 12 exemplify the present invention. Examples 13 to 21 are directed to comparisons of prior art type electrolyte systems and those of the present invention.

EXAMPLE 1—LiB($C_6H_5$)$_4$

Lithium tetraphenylboride was prepared in accordance with the teachings of Bhattacharyya et al, cited above, by reacting NaB($C_6H_5$)$_4$ with LiCl. A dry, solvent free salt was obtained at a yield of 91.4%. The salt was dissolved in dioxolane and was found to have a limited solubility. A saturated dioxolane solution contained about 1.14 moles of salt per liter of solvent. Because a low resistivity is important in any successful electrolyte system, specific resistivities were measured as a function of salt concentration in the solvent and the results are presented in Table I below.

EXAMPLE 2—TMED.LiB($C_2H_5$)$_3C_6H_5$

Tetramethylethylenediamine lithium triethylphenylboride represents the prior art electrolyte of the type described in U.S. Pat. No. 3,764,385. To a solution of triethylboron (19.66 g, 0.2 mol) in 250 ml of benzene was added dropwise 100 ml of a 2 M benzene solution of TMED.LiC$_6$H$_5$. After stirring overnight, the solution was warmed to 50° C. for 45 minutes. Solvent removal on a vacuum rotary evaporator gave TMED.-LiB($C_2H_5$)$_3C_6H_5$ as a white solid.

Analysis: Calculated for $C_{18}H_{36}N_2BLi$—C, 72.49; H, 12.17 and N, 9.39%. Found—C, 72.15; H, 11.99 and N, 8.94%.

Specific resistivities of the compound of Example 2 in dioxolane as a function of TMED.LiB($C_2H_6$)$_3C_6H_5$ concentration expressed as moles complex per liter solvent were obtained. The results are given in Table I below.

TABLE I

SPECIFIC RESISTIVITIES OF PRIOR ART LITHIUM SALTS IN DIOXOLANE

| Concentration (molal) | Specific Resistivity (Ohm Cm) | |
|---|---|---|
| | Example 1 | Example 2 |
| 0.5 | 320 | — |
| 1.0 | 266 | 224 |
| 2.0 | — | 238 |
| 3.0 | — | 331 |

EXAMPLE 3—LiB($C_6F_5$)$_4$

This prior art compound is prepared from B($C_6F_5$)$_3$ and $C_6F_5Li$ according to the procedure of Massey and Park, *J. Organometallic Chemistry*, 2, 245 (1964). An NMR spectrum of a weighed amount of this material shows the product to be a 1:1 complex with diethylether.

In order to test the electrolytic capability of this prior art compound, the material is dissolved in dioxolane at various concentrations and the specific resistivities of the solutions are measured as above, i.e., using a Barnstead Model PM-70CB Conductivity Bridge and a Yellow Springs Instrument Co. Model YSI 3403 Conductivity Cell having a cell constant of 1.0 cm$^{-1}$. The results presented in Table II demonstrate that this compound could be used as an organic electrolyte.

TABLE II

SPECIFIC RESISTIVITY OF LiB($C_6F_5$)$_4$ IN DIOXOLANE

| Concentration (Molal) | Resistivity (ohm cm) |
|---|---|
| 1.39 | 210 |
| 0.91 | 195 |
| 0.69 | 207 |
| 0.45 | 219 |
| 0.23 | 325 |

EXAMPLE 4—LiB($C_6H_5$)$_3C_6F_5$

To a 250 ml flask, containing a magnetic stirrer bar and fitted with a dropping funnel and N$_2$ inlet, is charged 10 g (40.5 mmole) of bromopentafluorobenzene and 60 ml of dry pentane. After cooling under dry N$_2$ to below −70° C. by means of a Dry-Ice acetone bath, a solution of butyllithium (27 ml, 1.5 molar) in hexane is added dropwise with stirring over 30 minutes. Triphenylboron (10 g, 41 mmole), contained in a gas tight syringe, is then added in portions through a rubber sleeve connected to one joint on the reaction flask. The slurry produced is stirred at −78° C. for 3 hours then is allowed to warm to room temperature overnight. Filtration affords 16.0 g of fine white powder (theory 17.3 g). A 0.134 g sample of this solid is dissolved in 0.703 g of dioxolane and an NMR spectrum of the resulting solution is obtained. The spectrum shows one broad multiplet centered around 7.6 ppm (~9H) and another centered around 7.0 ppm (~6H). The ratio of dioxolane protons to aromatic protons is 13.5 (calc. based on LiB($C_6H_5$)$_3C_6F_5$, 12.1). A 10 g sample of this solid is dissolved in excess dioxolane and a small amount of gel like material 1.6 g (final dry weight) is filtered from the clear, pale yellow solution. The latter is concentrated to yield 10.1 g of a soft yellow solid. A portion of this material is dissolved in dioxolane to give a 0.85 molal solution as determined by NMR analysis; the Specific Resistivity of this solution, determined in accordance with the procedure of Examples 1 through 3, is 419 ohm cm.

EXAMPLE 5—LiB($C_6F_5$)$_3$($CH_3$)

To a solution of 10.2 g (20 mmole) tris-(pentafluorophenyl)boron in 200 ml of benzene is added 0.44 g (20 mmole) of dry, low halide, methyllithium. Dissolution of the $CH_3Li$ occurs rapidly. After several days a solid forms which is isolated by filtration and washed with warm hexane. The final product (5 g) has a melting point of 193°–6° C.

EXAMPLE 6—LiB($C_6F_5$)$_3$($CH_3$).diethylether

To a solution of 4.06 g (8 mmole) tris-(pentafluorophenyl)boron in 150 ml of dry pentane is added 4.9 ml of methyllithium (1.7 M in diethylether). Stirring overnight at room temperature results in the formation of two liquid phases. These are separated and the lower viscous phase is washed several times with pentane. The resulting material is heated at 60°–90° C. under vacuum to give 3.5 g of waxy solid. An NMR spectrum of this solid in dioxolane shows a broad multiplet at 0.52 ppm assigned to the boron $CH_3$ (3H), a quartet at 3.6 ppm assigned to the ether methylene, and a triplet at 1.15 ppm for the ether methyl group (6H), features which suggest solvation of the LiB($C_6F_5$)$_3$($CH_3$) with the diethylether.

This compound is tested in accordance with the above procedure. The results presented in Table III demonstrate that this compound is useful as an organic electrolyte.

TABLE III

SPECIFIC RESISTIVITY OF
LiB($C_6F_5$)$_3$($CH_3$) . DIETHYLETHER IN DIOXOLANE

| Concentration (molal) | Resistivity (ohm cm) |
|---|---|
| 2.0 | 236 |
| 1.5 | 193 |
| 1.0 | 154 |
| 0.75 | 155 |
| 0.5 | 155 |

EXAMPLE 7—LiB($C_6F_5$)$_3$($C_4H_9$)

A solution containing 4.1 mmole of butyllithium in hexane is added dropwise to 2 g (3.9 mmole) of tris-(pentafluorophenyl)boron dissolved in 125 ml of dry pentane. Precipitation of the product begins immediately. After stirring overnight the solid is filtered and washed with pentane to give 2.36 g (quantitative) of salt, mp 185°–7° C. An NMR spectrum of this salt in dioxolane shows butyl resonances at 0.83 ppm (apparent doublet, $CH_3$) superimposed on a methylene multiplet spanning 0.6–1.5 ppm.

This compound is tested in accordance with the above procedure. The results presented in Table IV demonstrate that this compound is useful as an organic electrolyte.

TABLE IV

SPECIFIC RESISTIVITY OF
LiB($C_6H_5$)$_3$($C_4H_9$) IN DIOXOLANE

| Concentration (molal) | Resistivity (ohm cm) |
|---|---|
| 1.5 | 288 |
| 1.0 | 190 |
| 0.75 | 175 |
| 0.5 | 188 |

EXAMPLE 8—LiB($C_6F_5$)$_3$F

To a solution of 5 g of tris-(pentafluorophenyl) boron in 50 ml of anhydrous dimethoxyethane was added 2.6 g of dry lithium fluoride. The reaction was refluxed for four days, under an inert atmosphere. Excess lithium fluoride was removed from the cooled reaction by filtration and the solvent was removed at reduced pressure to yield the LiB($C_6F_5$)$_3$F product. The specific resistivity of a one molal dimethoxyethane solution of the salt was found to be about 180 ohm cm.

EXAMPLE 9—LiB($C_6H_4$—p—$CH_3$)$_3C_6F_5$

A solution of 9.94 g of tris-(p-tolyl)boron in 100 ml of toluene was added dropwise to a solution of pentafluorophenyl lithium [from 10 g of pentafluoro bromobenzene and 25.3 ml of butyl lithium (1.6 M in hexane) in 250 ml of diethyl ether, according to the teachings of Massey et al, cited above] at −70° C. The reaction was allowed to continue overnight at ambient temperature. The LiB($C_6H_4$-p—$CH_3$)$_3C_6F_5$ salt was isolated and purified by filtration, dissolution in toluene, filtration, and removal of the toluene at reduced pressure. The salt is a white material, mp, 193°–7° C., whose proton NMR spectrum exhibits the predicted AB pattern for the aromatic proton resonances and singlet for the paramethyl group, in an area ratio of 4:3.

EXAMPLE 10—LiB($C_6H_4$—p—$CF_3$)$_4$

To a rapidly stirred suspension of 10.8 g of magnesium chips and 10.3 g of lithium tetrafluoroboride in 600 ml of diethyl ether was added 10 ml of a solution of 100 g of p-bromobenzotrifluoride in 100 ml of diethyl ether. When the reaction started, as indicated by an exotherm, the reaction temperature was lowered to 18° and held there during the addition of the remainder of the bromobenzotrifluoride-ether solution. After an additional hour the reaction was poured into ice and made basic with lithium hydroxide. The ether phase was evaporated to dryness dissolved in 400 ml of water, extracted with n-hexane, charcoal treated, and reacted with an excess of dilute ammonium hydroxide. Ammonium-tetra-(p-trifluoromethylphenyl)-boride[$NH_4B$($C_6H_4$—p—$CF_3$)$_4$] precipitated as a white solid (wt. 24.2 g) mp, 204°–6° C. (MeOH/$H_2O$).

The ammonium salt was added to a stirred suspension of 4 equivalents of lithium hydride in 250 ml of dioxolane, and stirred at refluxed until evolution of ammonia ceased. The cooled reaction was filtered and concentrated at reduced pressure, until crystallization occurred. The salt, filtered and dried, had the composition, LiB($C_6H_4$—p—$CF_3$)$_4$ solvated with 4 parts dioxolane, mp, 155–8 (dioxolane/$\phi CH_3$). A 1.5 molal solution of this salt in dioxolane: dimethoxyethane (70:30) gave a specific resistivity value of 209 ohm cm.

EXAMPLE 11—LiB($C_6H_4$—m—$CF_3$)$_4$

Butyl lithium, 275 ml (1.6 M in hexane) was added, dropwise, to 100 g of m-bromobenzotrifluoride in 800 ml of diethyl ether cooled to −10° C. during the course of 1 hour. After an additional hour at ambient temperature, 10.2 ml of freshly distilled boron trifluoride etherate was added dropwise. The reaction was allowed to proceed for 2 hours at ambient temperature and poured into 600 ml of ice. After the ether layer was separated and evaporated at reduced pressure the residue was dissolved in water and extracted twice with n-hexane. The aqueous phase was heated to 45° C. and reacted with excess dilute aqueous trimethylamine. The precipitated trimethylammonium tetra(m-trifluoromethylphenyl) boride [$(CH_3)_3NHB(C_6H_4$—m—$CF_3)_4$] was filtered, washed with water and recrystallized from methanol-water, yield 30 g, mp, 149°-154° C.

The amine salt, 25.6 g, was then heated at reflux in 230 ml of methanol, containing 3 g of lithium methoxide until the evolution of trimethylamine ceased. Methanol was removed at reduced pressure, the residue dissolved in dioxolane, filtered, and the dioxolane evaporated to achieve the desired molar concentration of LiB($C_6H_4$—m—$CF_3$)$_4$ salt.

This LiB($C_6H_4$—m—$CF_3$)$_4$ compound was tested in accordance with the procedure of Examples 1 through 3 above. The measured Resistivity values recorded in Table V below demonstrate the utility of this compound as an organic electrolyte.

TABLE V
SPECIFIC RESISTIVITY OF LiB($C_6H_4$-m-$CF_3$)$_4$ IN DIOXOLANE

| Concentration (molal) | Resistivity (ohm cm) |
|---|---|
| 1.3 | 536 |
| 0.79 | 436 |
| 0.57 | 396 |
| 0.45 | 411 |
| 0.38 | 437 |
| 0.32 | 469 |
| 0.22 | 594 |

EXAMPLE 12-LiB($C_6H_4$—p—F)$_4$

In the manner detailed in Example 11, p-bromofluorobenzene was converted, in 63% yield, to trimethylammonium-tetra(p-fluorophenyl) boride, [$(CH_3)_3NHB(C_6H_4$—p—F)$_4$], mp, 170°-1° C.

The ammonium salt, 16 g, was heated at reflux with 1.8 g of lithium hydride in 100 ml of dioxolane until trimethylamine evolution ceased. The cooled reaction was filtered and the dioxolane evaporated under vacuum. The salt was isolated, 13.8 g, as a white solid having the composition LiB($C_6H_4$—p—F)$_4$.4 dioxolane, mp 128°-31°.

This LiB($C_6H_4$—p—$F_4$)$_4$ compound was tested in accordance with the procedure above. The measured Resistivity values recorded in Table VI below demonstrate the utility of this compound as an organic electrolyte.

TABLE VI
SPECIFIC RESISTIVITY OF LiB($C_6H_4$-p-F)$_4$ IN DIOXOLANE

| Concentration (molal) | Resistivity (ohm cm) |
|---|---|
| 0.63 | 230 |
| 0.58 | 233 |
| 0.53 | 239 |
| 0.44 | 256 |
| 0.38 | 275 |
| 0.29 | 328 |
| 0.23 | 385 |
| 0.15 | 583 |
| 0.09 | 969 |
| 0.03 | 3130 |

EXAMPLES 13 THROUGH 21

These examples are directed to the testing of various TMED-complexed prior art electrolyte-containing cells (Examples 13 through 16) and present invention electrolyte-containing cells (Examples 17 through 21).

The test cells contained a lithium anode of lithium ribbon pressed on expanded nickel or tantalum screen. The cathode was a porous cake of a mixture of $TiS_2$ and Teflon (90-95% $TiS_2$ and 5-10% Teflon) pressed onto an expanded nickel, tantalum or titanium screen or pressed onto a piece of carbon felt. The anode and cathode were separated by placing the anode and cathode in microporous polypropylene bags sold under the name "Celgard" by Celanese Corporation of America, New York. A glass mat was also placed between the anode and the cathode. The cells were also provided with a reference lithium electrode of lithium ribbon pressed on a tantalum or nickel screen. The reference was also in a microporous polypropylene bag and separated from the cathode by a glass mat. The reference electrode was located on the side of the cathode opposite the anode.

The results of the tests are set forth in Table VII below. As can be seen, most of the electrolytes of the present invention are at least as good as, and in many cases better than, the TMED-complexed electrolytes. Thus, it was surprisingly discovered that the prior art complexing requirements were, in fact, not necessary to obtain advantageous electrolyte systems.

TABLE VII
TEST CELL RESULTS FOR LITHIUM SALT-CONTAINING ELECTROLYTES[1]

| Example | Salt | % Primary | Theor. mA-Hrs. | Accumulated A-Hrs/g | F.O.M. | Discharge Rate mA | # Cycles | Cathode Grid |
|---|---|---|---|---|---|---|---|---|
| 13 | 1.5 m'TMED . LiB($CH_3$)$_4$ | 56 | 275 | 1.14 | 4.8 | 32.5 | 19 | Ta |
|  |  | 59 | 184 | 1.27 | 5.3 | " | 33 | Ta |
| 14 | 1.5 m'TMED . LiB($CH_3$)$_4$ | 66 | 123 | 4.1 | 17.2 | " | 47 | C |
|  |  | 66 | 120 | 4.8 | 20.2 | " | 42 | C |
| 15 | 2 m'TMED . LiB($C_2H_5$)$_3C_4H_9$ | 63 | 234 | 1.41 | 5.9 | " | 21 | Ta |
|  |  | 61 | 226 | 1.24 | 5.2 | " | 42 | Ta |
| 16 | 2 m'TMED . LiB($C_4H_9$)$_4$ | 40 | 142 |  |  | " | 32 | Ni |
|  |  | 40 | 148 | 1.92 | 8.0 | " | 43 | Ni |
| 17 | 1 m'LiB($C_6F_5$)$_3CH_3$ | 100 | 176 | 0.71 | 3.5 | 8.8 | 5 | Ti |
| 18 | 2.0 m'LiB($C_6F_5$)$_3CH_3$ | 100• | 95 | 1.79 | 6.0 | 4.8 | 13 | Ti |
|  |  | 100 | 91 | 1.81 | 6.4 | 4.9 | 32 | Ti |
| 19 | 0.7 m'LiB($C_6F_5$)$_3C_4H_9$ | 95 | 198 | 1.02 | 2.5 | 9.9 | 7 | Ti |

TABLE VII-continued
TEST CELL RESULTS FOR LITHIUM SALT-CONTAINING ELECTROLYTES[1]

| Example | Salt | % Primary | Theor. mA-Hrs. | Accumulated A-Hrs/g | F.O.M. | Discharge Rate mA | # Cycles | Cathode Grid |
|---|---|---|---|---|---|---|---|---|
| 20 | 1.5 m'LiB($C_6H_5$-p-$CF_3$)$_4$ | 85 | 180 | 2.93 | 8.8 | 6.5 | 20 | Ti |
| 21 | 1.5 m'LiB($C_6F_5$)$_3$F . DME | 60 | 84 | 1.15 | 4.5 | 13.0 | 10 | Ti |

[1]Definition of column headings:
% Primary - the material utilization of the cell in the first discharge as calculated by the number of milliamps hrs of discharge divided by the theoretical amount possible determined by the weight of $TiS_2$ present.
Theor. (mA-Hrs) - mA-Hrs possible in cell from wt. of $TiS_2$.
Accumulated A-Hrs./g. - (Accumulated Amp-Hr./g.) - is equal to the number of cycles achieved to the material utilization (M.U.) at the termination of the testing multiplied by the average M.U. multiplied by the theoretical amp-hrs./g. of $TiS_2$.
Accumulated A-hr/g = # cycles × average M.U. × theoretical A-hr./g. $TiS_2$.
F.O.M. (Figure of Merit) - th accumulatred A-hrs./g. divided by the theoretical A-hr./g. $TiS_2$.
Discharge Rate - total current during discharge of cells. All cathodes were 1 in.$^2$ in area.
Cycles - the total number of charge-discharge cycles that the cell was subjected to and were included in the calculations of the figure of merit (FOM).
Cathode Grid - the material used as the electronic collector material of the cathode.

What is claimed is:

1. A composition, comprising one or more haloorganometallic lithium salt complexes having the formula:

$$LiMR_nX_i$$

wherein M is a metal selected from the group consisting of Zn, Cd, B, Al, Ga, In, Tl, Sn (stannous), P and As, wherein R represents n number of radicals which may be the same or different and which are inertly substituted or otherwise unsubstituted haloorganic radicals selected from the group consisting of haloorganic radicals selected from the group consisting of halogenated alkyl radicals having 2 to 8 carbon atoms, halogenated aryl radicals having 6 to 18 carbon atoms, and halogenated alkaryl and halogenated aralkyl radicals having 7 to 50 carbon atoms, subject to the proviso that the radicals are not alpha halogenated, wherein X represents i number of radicals which may be the same or different and which are selected from the group consisting of halogens, alkyl radicals having 1 to 8 carbon atoms, aryl radicals having 6 to 18 carbon atoms, and alkaryl and aralkyl radicals having 7 to 50 carbon atoms, wherein n and i are numerical values which are zero or positive integers, and wherein the sum of n plus i is equal to one plus the valence of the metal M, subject to the provisos that when n is zero, at least one X is an organic radical, and when i is zero, not all R radicals are perhalogenated aryl radicals.

2. The composition of claim 1 wherein the R radicals are selected from the group consisting of halogenated alkaryl and halogenated aralkyl radicals having 7 to 25 carbon atoms, and halophenyl radicals.

3. The composition of claim 2 wherein the X radicals are selected from the group consisting of halogens, alkyl radicals having 1 to 6 carbon atoms, and the phenyl radical.

4. The composition of claim 3 wherein M is a metal selected from the group consisting of B, Al, Tl, P and As.

5. The composition of claim 4 wherein the X radicals are selected from the group consisting of fluorine, chlorine and the methyl radical.

6. The composition of claim 5 wherein M is a metal selected from the group consisting of B, Al and P.

7. The composition of claim 6 wherein M is boron.

8. The composition of claim 1 wherein the R radicals are selected from the group consisting of halogenated alkaryl radicals having 7 to 15 carbon atoms.

9. The composition of claim 8 wherein the X radicals are selected from the group consisting of halogens, alkyl radicals having 1 to 6 carbon atoms, and the phenyl radical.

10. The composition of claim 9 wherein M is a metal selected from the group consisting of B, Al, Tl, P and As.

11. The composition of claim 10 wherein the X radicals are selected from the group consisting of fluorine, chlorine and the methyl radical.

12. The composition of claim 11 wherein M is a metal selected from the group consisting of B, Al and P.

13. The composition of claim 12 wherein M is boron.

14. An electrolyte composition, comprising:
(a) an organic solvent selected from the group consisting of inertly substituted and unsubstituted ethers, esters, alkylene carbonates, amines, amides, lactones, sulfones, organic sulfites, organic sulfates, orthoformates, alkylhaloformates, polyamines, organic nitro compounds and organic nitrites; and
(b) one or more electrolytically active alkali metal salt complexes including haloorganometallic lithium salt complexes having the formula:

$$LiMR_nX_i$$

wherein M is a metal selected from the group consisting of Zn, Cd, B, Al, Ga, In, Tl, Sn (stannous), P and As, wherein R represents n number of radicals which may be the same or different and which are inertly substituted or otherwise unsubstituted haloorganic radicals selected from the group consisting of halogenated alkyl radicals having 2 to 8 carbon atoms, halogenated aryl radicals having 6 to 18 carbon atoms, and halogenated alkaryl and halogenated aralkyl radicals having 7 to 50 carbon atoms, subject to the proviso that the radicals are not alpha halogenated, wherein X represents i number of radicals which may be the same or different and which are selected from the group consisting of halogens, alkyl radicals having 1 to 8 carbon atoms, aryl radicals having 6 to 18 carbon atoms, and alkaryl and aralkyl radicals having 7 to 50 carbon atoms, wherein n and i are numerical values which are zero or positive integers, and wherein the sum of n plus i is equal to one plus the valence of the metal M, subject to the provisos that when n is zero, at least one X is an organic radical, and when i is zero, not all R radicals are perhalogenated aryl radicals.

15. The electrolyte composition of claim 14 wherein the R radicals are selected from the group consisting of halogenated alkaryl and halogenated aralkyl radicals having 7 to 25 carbon atoms, and halophenyl radicals.

16. The electrolyte composition of claim 15 wherein the X radicals are selected from the group consisting of halogens, alkyl radicals having 1 to 6 carbon atoms, and the phenyl radical.

17. The electrolyte composition of claim 16 wherein M is a metal selected from the group consisting of B, Al, Tl, P and As.

18. The electrolyte composition of claim 17 wherein the X radicals are selected from the group consisting of fluorine, chlorine and the methyl radical.

19. The electrolyte composition of claim 18 wherein M is a metal selected from the group consisting of B, Al, and P.

20. The electrolyte composition of claim 19 wherein M is boron.

21. The electrolyte composition of claim 20 wherein the R radicals are selected from the group consisting of halogenated alkaryl radicals having 7 to 15 carbon atoms.

22. The electrolyte composition of claim 21 wherein the X radicals are selected from the group consisting of halogens, alkyl radicals having 1 to 6 carbon atoms, and the phenyl radical.

23. The electrolyte composition of claim 22 wherein M is a metal selected from the group consisting of B, Al, Tl, P and As.

24. The electrolyte composition of claim 23 wherein the X radicals are selected from the group consisting of fluorine, chlorine and the methyl radical.

25. The electrolyte composition of claim 24 wherein M is a metal selected from the group consisting of B, Al and P.

26. The electrolyte composition of claim 25 wherein M is boron.

27. The electrolyte composition of claim 14 wherein said organic solvent is one or more ethers.

28. The electrolyte composition of claim 27 wherein the R radicals are selected from the group consisting of halogenated alkaryl and halogenated aralkyl radicals having 7 to 25 carbon atoms, and halophenyl radicals.

29. The electrolyte composition of claim 28 wherein the X radicals are selected from the group consisting of halogens, alkyl radicals having 1 to 6 carbon atoms, and the phenyl radical.

30. The electrolyte composition of claim 29 wherein M is a metal selected from the group consisting of B, Al, Tl, P and As.

31. The electrolyte composition of claim 30 wherein the X radicals are selected from the group consisting of fluorine, chlorine and the methyl radical.

32. The electrolyte composition of claim 31 wherein M is a metal selected from the group consisting of B, Al and P.

33. The electrolyte composition of claim 32 wherein M is boron.

34. The electrolyte composition of claim 33 wherein the R radicals are selected from the group consisting of halogenated alkaryl radicals having 7 to 15 carbon atoms.

35. The electrolyte composition of claim 34 wherein the X radicals are selected from the group consisting of halogens, alkyl radicals having 1 to 6 carbon atoms, and the phenyl radical.

36. The electrolyte composition of claim 35 wherein M is a metal selected from the group consisting of B, Al, Tl, P and As.

37. The electrolyte composition of claim 36 wherein the X radicals are selected from the group consisting of fluorine, chlorine and the methyl radical.

38. The electrolyte composition of claim 37 wherein M is a metal selected from the group consiting of B, Al and P.

39. The electrolyte composition of claim 38 wherein M is boron.

* * * * *